United States Patent [19]

Duffett

[11] Patent Number: Plant 5,736

[45] Date of Patent: May 6, 1986

[54] CHRYSANTHEMUM PLANT NAMED CITRON

[75] Inventor: William E. Duffett, Salinas, Calif.

[73] Assignee: Yoder Brothers, Inc., Barberton, Ohio

[21] Appl. No.: 636,853

[22] Filed: Aug. 1, 1984

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant named Citron characterized as to uniqueness by the combined characteristics of flat capitulum form, daisy capitulum type, light orange ray floret color, diameter across face of capitulum ranging from 5 to 7 cm. at maturity, uniform nine week flowering response; tall plant height when grown single stem, 17 to 23 cm. peduncles on open, normally terminal sprays, rapid development of green discs devoid of pollen, 13° C. minimum temperature tolerance for initiation and development of flowering buds, and a long duration of both leaves and flowers.

3 Drawing Figures

The present invention comprises a new and distinct cultivar of *Chrysanthemum morifolium,* Ramat., named Citron.

Citron is a product of a planned breeding program which had the objective of creating new chrysanthemum cultivars having low temperature tolerance for cut spray mum programs with daisy capitulum type, bronze ray floret color, eight to nine week flowering response, and the ability to produce commercially acceptable quality in year round programs. Such traits in combination were not present or needed improvement in previously available commercial cultivars.

Citron, identified as 80520004, was originated from a cross made by William E. Duffett in a controlled environment in Salinas, Calif., in 1979. The female parent was Flash, identified as 77179040, a bronze daisy disclosed by U.S. Plant Pat. No. 5,202. The male parent of Citron was identified as 77358001, an unnamed bronze daisy seedling.

Citron was discovered and selected as one flowering plant within the progeny of the stated cross by William E. Duffett on Nov. 6, 1981 in a controlled environment in Bogota, Colombia.

The first act of asexual reproduction of Citron was accomplished when vegetative cuttings were taken from the initial selection in January 1982 in a controlled environment in Bogota, Colombia by a technician working under formulations established and supervised by William E. Duffett through Fernando Jaramillo.

Horticultural examination of selected units initiated December 1982 has demonstrated that the combination of characteristics as herein disclosed for Citron are firmly fixed and are retained through successive generations of asexual reproduction.

Citron has not been observed under all possible environmental conditions. The phenotype may vary significantly with variations in environment such as temperature, light intensity, and day length. The following observations, measurements and comparisons describe plants grown in Bogota, Columbia under greenhouse conditions which approximate those generally used there in commercial practice.

The following traits have been repeatedly observed and are determined to be basic characteristics of Citron which in combination distinguish this chrysanthemum as a new and distinct cultivar:

1. Flat capitulum form.
2. Daisy capitulum type.
3. Light bronze ray floret color.
4. Diameter across face of capitulum ranging from 5 to 7 cm. at maturity.
5. Uniform nine week photoperiodic flowering response to short days.
6. Long peduncle length, ranging from 17 to 23 cm.
7. Tall plant height, requiring one long day week prior to short days to attain a flowered plant height of 104 to 110 cm. for year around flowerings.
8. Low temperature tolerance of 13° C. for initiation and development when grown in single stem cut spray programs with a continuous dark period of 12 hours.
9. High leaf and flower durability.

The accompanying photographic drawings show typical inflorescence and leaf characteristics of Citron, with the colors being as nearly true as possible with illustrations of this type. Sheet 1 is a color photograph of Citron grown as a single stem cut spray. Sheet 2 is a black and white photograph of three views of the inflorescence of Citron. Sheet 3 is a black and white photograph showing the upper surface and under surface of leaves of Citron at three stages of development (mature, intermediate and immature).

Of the many commercial cultivars known to the present inventor, the most similar in comparison to Citron is Bronze Marble, unpatented and commercially available.

Reference is made to attached Chart A which compares certain characteristics of Citron to those same characteristics of Bronze Marble. Citron develops a deeper color with a slower rate of oxidation to the yellow orange hue, has smaller capitulum diameter, taller plant height, and longer duration of leaves and flowers. Citron and Bronze Marble have similar capitulum type, form, response, low temperature tolerance, and peduncle length in the spray.

In the following description, color references are made to The Royal Horticultural Society Colour Chart. The color values were determined between 11:45 A.M. and 11:55 A.M. on Dec. 27, 1983 under 380 foot-candle light intensity at Salinas, Calif.

Classification:

*Botanical.*—Chrysanthemum morifolium, Ramat., cv CITRON.

*Commercial.*—Daisy cut spray mum.

I. INFLORESCENCE

A. Capitulum:

*Form.*—Flat.

*Type.*—Daisy.

*Diameter across face.*—5 to 7 cm.

B. Corolla of ray florets:

*Color (general tonality from a distance of three meters).*—Light orange.

*Color (upper surface).*—22A.

*Color (under surface).*—21B, 21C.

*Shape.*—Oblong.

C. Corolla of disc florets:

*Color (mature).*—154C.

*Color (immature).*—145A.

D. Reproductive organs:

*Androecium.*—Present disc florets only; no pollen.

*Gynoecium.*—Present both ray and disc florets.

II. PLANT

A. General appearance:

*Height.*—Tall; 104 to 110 cm. as a single stem flowering plant from a rooted cutting, with seven long days for year around flowering with a minimum nightly 12 hour continuous dark period.

B. Foliage:

*Color (upper surface).*—147A

*Color (under surface).*—147B.

*Shape.*—Deeply lobed and coarsely serrated.

C. Stem:

*Color.*—176A-B.

CHART A

COMPARISON OF CITRON AND BRONZE MARBLE

| | RAY FLORET | CAPITULUM FORM | SPRAY |
|---|---|---|---|

CHART A-continued

COMPARISON OF CITRON AND BRONZE MARBLE

| CULTIVAR | COLOR | AND TYPE | FORMATION |
|---|---|---|---|
| CITRON | LIGHT ORANGE | FLAT DAISY | 17 to 23 cm. PEDUNCLES |
| BRONZE MARBLE | LIGHT YELLOW ORANGE | FLAT DAISY | 15 to 24 cm. PEDUNCLES |

| CULTIVAR | DIAMETER ACROSS FACE OF CAPITULUM | PLANT HEIGHT | FLOWERING RESPONSE PERIOD |
|---|---|---|---|
| CITRON | 5 to 7 cm. | TALL 104 to 110 cm. | 9 WEEKS |
| BRONZE MARBLE | 7 to 8 cm. | MEDIUM 70 to 80 cm. | 9 WEEKS |

| CULTIVAR | LOW TEMPERATURE | DURABILITY |
|---|---|---|
| CITRON | LOW TO 13° C. | LEAF - HIGH (7–14 DAYS) FLOWER - HIGH (2–3 WEEKS) |
| BRONZE MARBLE | LOW TO 13° C. | LEAF - LOW (3–4 DAYS) FLOWER - HIGH (1–2 WEEKS) |

COMPARISONS MADE OF PLANTS GROWN AS SINGLE STEM CUT SPRAY MUMS WITH 7 LONG DAYS IN BOGOTA, COLOMBIA

I claim:

1. A new and distinct plant of *Chrysanthemum morifolium,* Ramat., named Citron, as described and illustrated, and particularly characterized as to uniqueness by the combined characteristics of flat capitulum form; daisy capitulum type; light orange ray floret color; diameter across face of capitulum ranging from 5 to 7 cm. at maturity; uniform nine week flowering response; tall plant height when grown single stem; 17 to 23 cm. peduncles on open, normally terminal sprays; rapid development of green discs devoid of pollen; 13° C. minimum temperature tolerance for initiation and development of flowering buds, and a long duration of both leaves and flowers.

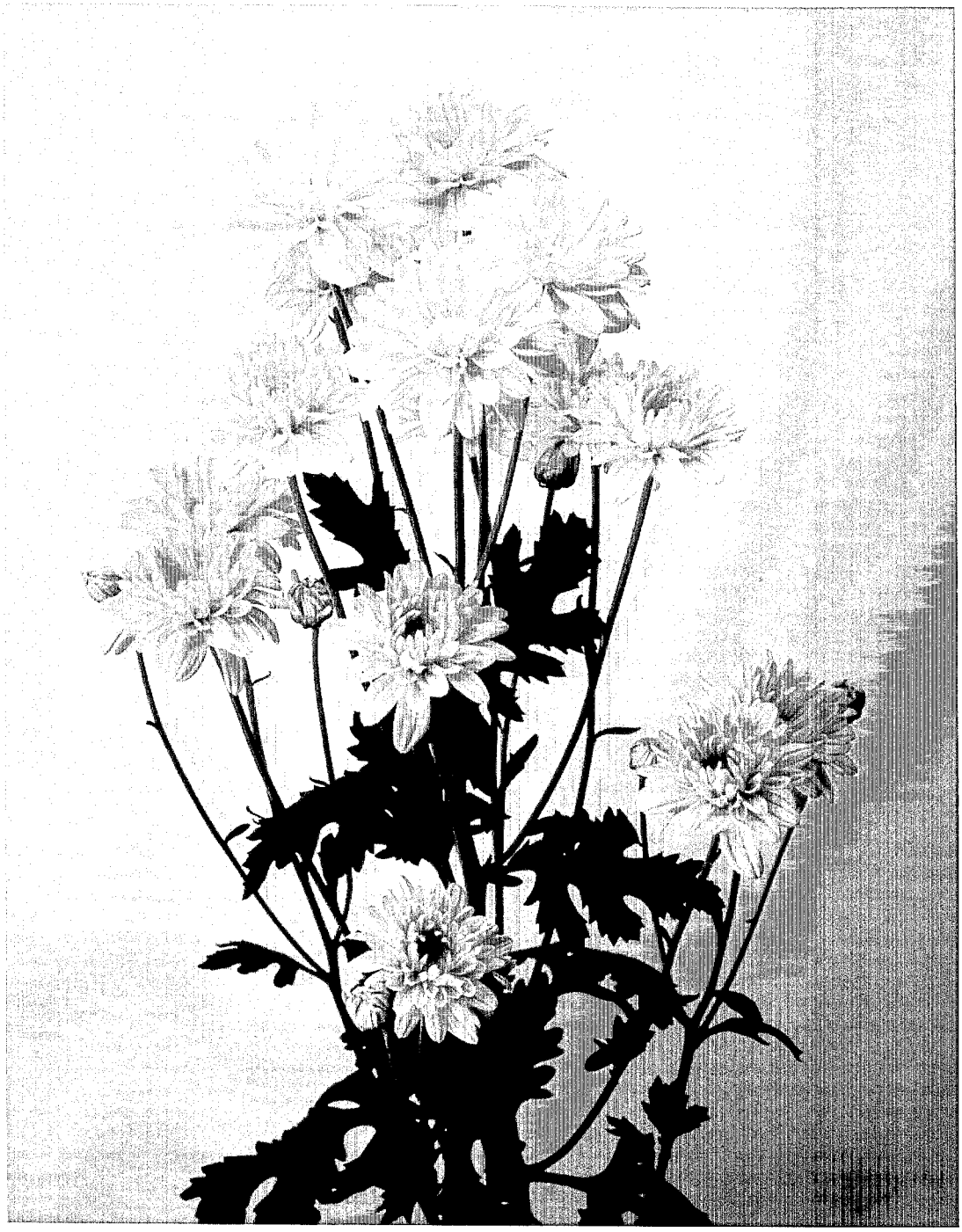

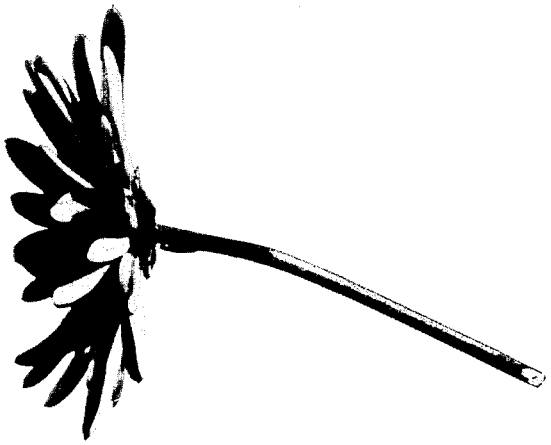
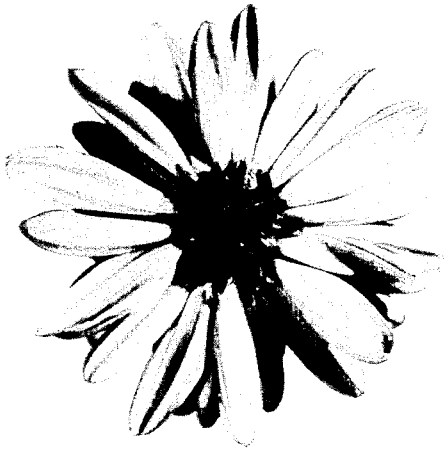
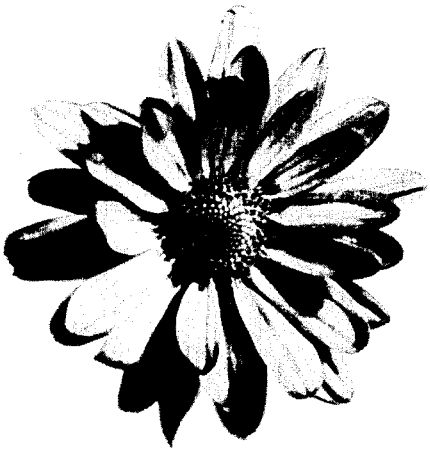

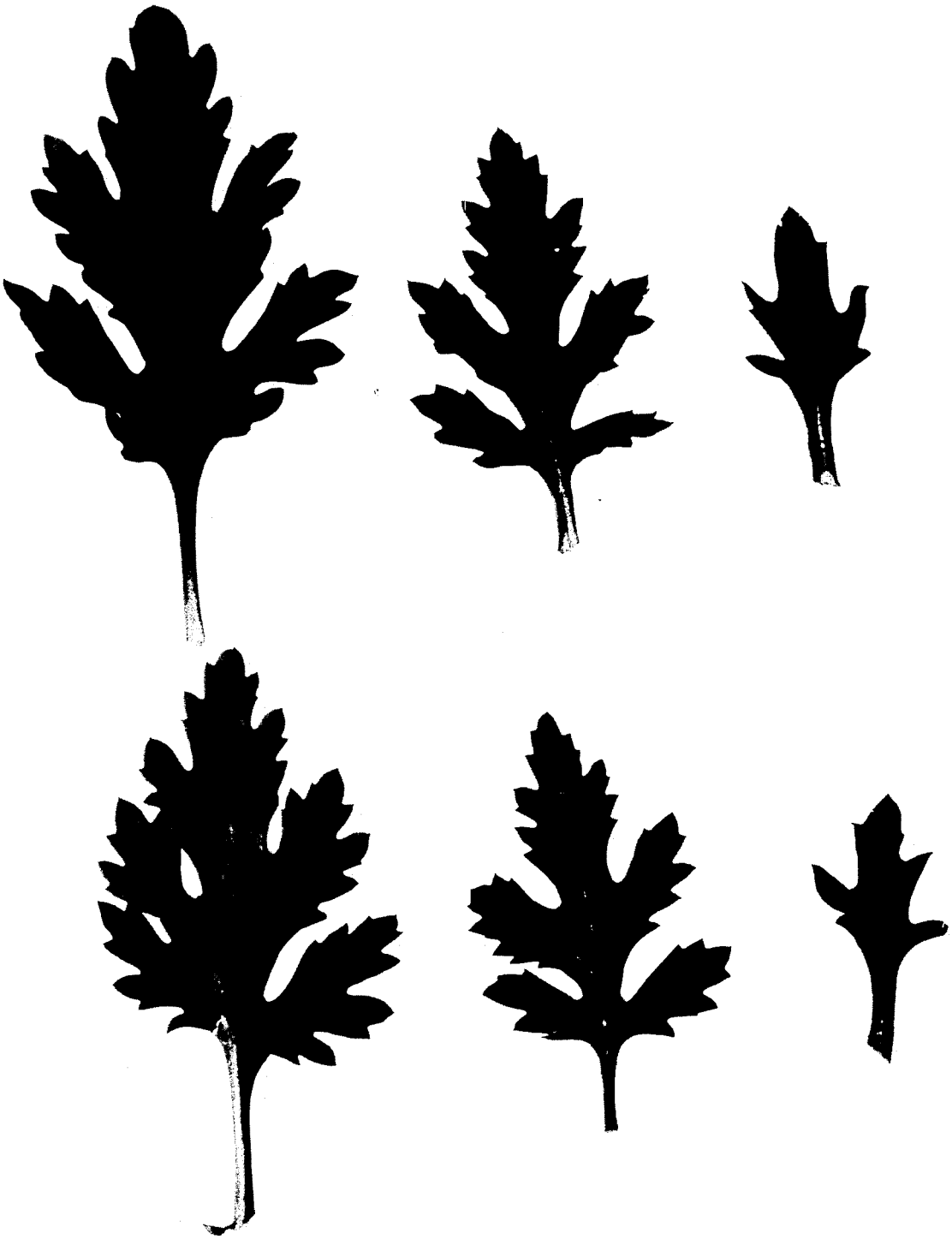

* * * * *